(12) United States Patent
Li et al.

(10) Patent No.: US 7,923,007 B2
(45) Date of Patent: Apr. 12, 2011

(54) BRAIN TISSUE DAMAGE THERAPIES

(75) Inventors: Hung Li, Taipei (TW); Woei-Cherng Shyu, Taipei (TW); Dah-Ching Ding, Hualien (TW); Shin-Zong Lin, Hualien (TW)

(73) Assignee: Academia Sinica, Taipei (TW)

( * ) Notice: Subject to any disclaimer, the term of this patent is extended or adjusted under 35 U.S.C. 154(b) by 727 days.

(21) Appl. No.: 11/462,426

(22) Filed: Aug. 4, 2006

(65) Prior Publication Data
US 2008/0274087 A1    Nov. 6, 2008

Related U.S. Application Data

(60) Provisional application No. 60/706,377, filed on Aug. 8, 2005.

(51) Int. Cl.
*A01N 63/00* (2006.01)
*A01N 65/00* (2009.01)
*A61K 48/00* (2006.01)
*C12N 5/071* (2010.01)

(52) U.S. Cl. ............... 424/93.7; 424/93.21; 424/93.1; 435/372

(58) Field of Classification Search .............. 424/93.7
See application file for complete search history.

(56) References Cited

U.S. PATENT DOCUMENTS

2002/0028510 A1 * 3/2002 Sanberg et al. ............ 435/368
2004/0136967 A1 * 7/2004 Weiss et al. ................ 424/93.7

OTHER PUBLICATIONS

Yang, Springer Semin. Immun., 26: 187-200, 2004.*
Kozlowska et al (2007, Stem Cells and Development, 16:481-488.*
Weiss, 2003, Experimental Neurology, 182:288-299.*
Lu et al., 2002, Cell Transplantation, 11:275-281.*
Chen et al., 2001, Stroke, 32:1005-1011.*
Rojewski, 2008, Tranfus Med Hemother, 35:168-184.*
Fink, JS et al, 2000; Cell Transplantation, 9:273-278.*
Mitchell et al., "Matrix Cells from Wharton's Jelly Form Neurons and Glia," *Stem Cells*, 21:50-60 (2003).
Wang et al., "Mesenchymal Stem Cells in the Wharton's Jelly of the Human Umbilical Cord," *Stem Cells*, 22:1330-1337 (2004).
Zhao et al., "Human Bone Marrow Stem Cells Exhibit Neural Phenotypes and Ameliorate Neurological Deficits after Grafting into the Ischemic Brain of Rats," *Experimental Neurology*, 174:11-20 (2002).

* cited by examiner

*Primary Examiner* — Valarie Bertoglio
(74) *Attorney, Agent, or Firm* — Occhiuti Rohlicek & Tsao LLP

(57) ABSTRACT

A cultured pluripotent animal cell that is CD13+, CD90+, and CD117−. Also disclosed are methods for making the cell and methods of treating a brain tissue damage and increasing the expression level of a neuraltrophic factor in a subject.

13 Claims, No Drawings

BRAIN TISSUE DAMAGE THERAPIES

RELATED APPLICATIONS

This application claims priority to U.S. Application Ser. No. 60/706,377, filed Aug. 8, 2005, the contents of which are incorporated herein in their entirety.

BACKGROUND

Brain tissue damage, resulting either from injuries or disorders (e.g., neurodegenerative and cerebrovascular diseases), are a leading cause of long-term disability. Due to their pluripotency, embryonic stem cells (ES cells) hold a great promise for treating brain tissue damage (Lindvall et al., 2004, Nat. Med., 10 Suppl:S42-50; and Taguchi et al., 2004, J. Clin. Invest.; 114(3):330-338). However, ethical and logistical considerations have hampered their use (Barinaga, 2000, Science, 287(5457):1421-1422; and Boer, 1994, J. Neurol., 242(1):1-13). There is a need for an alternative to ES cells in treating brain tissue damage.

SUMMARY

This invention is based, at least in part, on the unexpected finding that pluripotent, non-embryonic cells can be obtained and used to treat brain tissue damage.

Accordingly, one aspect of this invention features cultured pluripotent animal cells, e.g., human cells, that are CD13+, CD90+, and CD117−. The cells can have one or more additional marker characteristics shown in Table 1, Example 1 below. Preferably, they have all of the marker characteristics shown in Table 1.

The invention also features a method of producing the above-described pluripotent animal cells. The method includes obtaining connective tissue from the umbilical cord of an animal (e.g., the Wharton's jelly); culturing the connective tissue to allow cells therein to migrate out of the connective tissue; and enriching pluripotent cells among the migrated cells. To allow cells to migrate out of the connective tissue, the connective tissue is cultured for 5-7 days. The pluripotent cells are CD13+, CD90+, and CD117−. They can have one or more additional marker characteristics shown in Table 1.

Another aspect of the invention features a method of treating brain tissue injury, e.g., ischemic injury. The method includes administering to a subject in need thereof an effective amount of a plurality of the above-described pluripotent cells.

The invention also features a method of treating a neurodegenerative disease. The method includes identifying a subject suffering from or being at risk for developing a neurodegenerative disease, and administering to the subject an effective amount of pluripotent animal cells, each of which is the cell described above. Examples of the neurodegenerative disease include Parkinson's disease, Alzheimer's disease, Spinocerebellar disease, or Huntington's disease.

The invention further features a method of increasing the expression level of a neurotrophic factor in the brain of a subject. The method includes administering to a subject indeed thereof an effective amount of pluripotent animal cells. Examples of the neurotrophic factor include brain-derived neurotrophic factor, glial-cell line derived neurotrophic factor, nerve growth factor, stromal cell derived factor-1, transforming growth factor, fibroblast growth factor, and vascular endothelial growth factor.

In all of the above-described methods, the cells are administered (e.g., intracerebrally) to a subject at $1 \times 10^4$ to $1 \times 10^7$/time, preferably at $1 \times 10^5$ to $5 \times 10^6$/time, or more preferably at $5 \times 10^5$ to $2 \times 10^6$/time. To minimize or avoid host rejections, the cells are preferably autologous to the subject.

"Treating" refers to administration of a composition (e.g., a cell composition) to a subject, who is suffering from or is at risk for developing brain tissue damage or a disorder causing such damage, with the purpose to cure, alleviate, relieve, remedy, prevent, or ameliorate the damage/disorder, the symptom of the damage/disorder, the disease state secondary to the damage/disorder, or the predisposition toward the damage/disorder. An "effective amount" refers to an amount of the composition that is capable of producing a medically desirable result in a treated subject. The treatment method can be performed alone or in conjunction with other drugs or therapies.

The details of one or more embodiments of the invention are set forth in the description below. Other features, objects, and advantages of the invention will be apparent from the description and from the claims.

DETAILED DESCRIPTION

It has been suggested that ES cells can be used to regenerate neuronal or glial cells in the brain and thereby treat brain tissue damage. However, ethical and logistical considerations have hampered the use of ES cells. Bone marrow-derived mesenchymal stem cells (MSCs) represent a promising alternative. Nonetheless, this alternative is not always acceptable due to the high risk of viral infection and the significant decreases in cell number and proliferation/differentiation capacity with age.

The present invention relates to isolating and using umbilical cord-derived mesenchymal stem cells (UCMSCs) in treating brain tissue damage. Like ES cells, UCMSCs possess potential to differentiate into various cells, including neuronal cells or glial cells. They therefore can be used to regenerate the cells for treating brain tissue damage. As shown in example 1 below, UCMSCs can be easily isolated, maintained and expanded in vitro, and induced to differentiation using routine technical approaches. In addition, after grafting UCMSCs into mice, there is no evidence of mitotically active cells, teratomas, or malignant growth. These cells can be used for transplantation in treating stroke, head injury, or neurodegeneration without the above-mentioned concerns. Due to these advantages, the cells represent an alternative to other pluripotent cells. In a preferred embodiment of this invention, human UCMSCs (HUCMSCs) are isolated form the Wharton's jelly (WJ).

Wharton's jelly is a gelatinous connective tissue from the umbilical cord and composed of myofibroblast-like stromal cells, collagen fibers, and proteoglycans (Kobayashi et al., 1998, Early Hum Dev 51, 223-33). The cells from the Wharton's jelly of porcine umbilical cord could be cultured and maintained for more than 100 population doublings and continue to grow vigorously (Weiss, et al. 2003, Exp Neurol 182, 288-99). Immuno-histochemical and ultrastructual investigation reveals that cells from the Wharton's jelly possess characteristics of stromal cells, and show differentiated distribution pattern of various cytoskeletal and extracellular matrix proteins (Nanaev et al. 1997, Placenta 18, 53-64).

To prepare HUCMSCs, one can use the method described in Example 1 below. In general, umbilical cords of gestational age between 37 and 40 weeks can be used. Care should be taken to avoid contamination. The umbilical cord tissues are washed and cut along the midline direction. Preferably, the vessels of umbilical artery, vein, and outlining membrane are removed from the Wharton's jelly. Subsequently, the Wharton's jelly is extensively cut into many pieces, e.g., smaller than 0.5 cm$^3$, and dissociated by digestion of collagenase. The resulting explants are cultured in an undifferentiating medium, e.g., DMEM containing 10% human cord blood serum and left undisturbed for 5-14 days, e.g., 5-7 days, to allow migration of cells from the explants. Within this period, adherently growing cells of spindle-shaped morphology migrate from the explants. They can be fed with the medium twice weekly and passed as necessary.

To confirm that the cells are indeed HUCMSCs, HUCMSC specific surface molecules are examined on passage 4-8 generations of the above-described cells by, e.g., flow cytometric analysis or other standard immunochemical analysis. Antibodies against the antigens listed in Table 1 below can be used. They can be conjugated with suitable labels, such as fluorescein isothiocyanate (FITC), phycoerythrin (PE), or quantum dots. HUCMSCs, which are negative for CD 34, CD45, and CD117, but positive for CD29, CD44, and CD49, can be further enriched using flow cytometry.

The enriched HUCMSCs are then tested by standard techniques. To investigate the differentiation potential of HUCMSCs, fifth to tenth-passage cells can be induced to form neuro-glial cells, osteocyte, and adipocyte by methods known in the art. For example, HUCMSCs are passed and cultured to confluence, shifted to an osteogenic medium or an adipogenic medium, and incubated for suitable time (e.g., 3 weeks). The differentiation potential for osteogenesis is assessed by the mineralization of calcium accumulation, which can be visualized by von Kossa staining. To examine adipogenic differentiation, intracellular lipid droplets can be stained by Oil Red O and observed under a microscope. For neural differentiation, HUCMSCs can be incubated in a neurogenic medium for suitable duration (e.g., 7 days), and then subjected to serum depletion and incubation of β-mercaptoethanol. After differentiation, HUCMSCs exhibit the morphology of refractile cell body with extended neuritelike structures arranged into a network. Immunocytochemical stain of lineage specific markers can be further conducted to confirm neural differentiation. Examples of the markers include neuron specific class III β-tubulin (Tuj-1), neurofilament, and GFAP.

The immunophenotype of the clonally expanded cells is consistent with that reported for bone marrow MSCs. Under appropriate induction conditions, the HUCMSCs can differentiate into adipocytes, chondrocytes, and cells in the osteogenic lineages in vitro. In addition, these cells are able to differentiate into neuroglial cells under the above-described induction conditions. Furthermore, cerebrally ischemic rats receiving intracerebral HUCMSCs transplantation exhibit significantly improved neurological function than vehicle-treated control rat. The results indicate that intracerebrally administered HUCMSCs can enter brain, survive, migrate, and improve functional recovery of stroke. In fact, transplanted HUCMSCs are seen to differentiate into glial cells (GFAP+), neuron (Nestin+, MAP-2+ and Neu-N+), and vascular endothelial cells (vWF+) to enhance neuroplastic effect in ischemic brain. Cortical neuronal activity as evaluated by Proton MR spectroscopy ($^1$H-MRS) is also much increased on transplantation group in comparison to control. In addition, significantly increased modulation of neurotrophic factor expression in the ischemic hemisphere is also found in the HUCMSCs transplantation group.

The above-described HUCMSCs can be propagated in a non-differentiating medium culture for more than 40 population doublings without indications of spontaneous differentiation, senescence, morphological changes, increased growth rate, or changes in ability to differentiate into neurons.

The HUCMSCs thus confirmed can be stored by standard methods or can be administered intracerebrally to a subject in need thereof. In general, $1\times10^4$ and $1\times10^7$ (e.g., $1\times10^5$ to $5\times10^6$ and more preferably $5\times10^5$ to $2\times10^5$) cells are administered. Multiple sites can be used depending on the site and nature of particular damage. Example 2 below describes approximate coordinates for administering cells in a rat ischemia model. Coordinates for other disorders in other species can be determined accordingly based on comparative anatomy.

Within the scope of this invention is a method of treating brain tissue damage or alleviate the symptom of the disorder in a subject. The method includes identifying a subject suffering from or being at risk for developing brain tissue damage. The subject can be a human or a non-human mammal, such as a cat, a dog, or a horse. Examples of the brain tissue damage includes those caused by a cerebral ischemia (e.g., chronic stroke) or a neurodegenerative disease (e.g., Parkinson's disease, Alzheimer's disease, Spinocerebellar disease, or Huntington's disease). A subject to be treated can be identified by standard techniques for diagnosing the conditions or disorders of interest. The treatment method entails administering to a subject in need thereof an effective amount of the above-described HUCMSCs.

The therapeutic effects of cells can be accessed according to standard methods (e.g., those described in Example 2 below). To confirm efficacy in promoting cerebrovascular angiogenesis, one can examine the subject before and after the treatment by standard brain imaging techniques, such as computed tomography (CT), Doppler ultrasound imaging (DUI), magnetic resonance imaging (MRI), and proton magnetic resonance spectroscopy ($^1$H-MRS). For example, $^1$H-MRS represents a non-invasive means to obtain biochemical information correlated to brain metabolic activity (Lu et al., 1997, Magn. Reson. Med. 37, 18-23). This technique can be applied to evaluate the metabolic changes involved in cerebral ischemia with or without stem cell transplantation. For example, it can be used to study the N-acetylaspartate (NAA) concentration in the brain, a marker of neuronal integrity. Although NAA redistribution and trapping in neuronal debris limits its use as a quantitative neuronal marker, decreases in brain NAA concentration in cerebral ischemia can be considered as an index of neuronal loss or dysfunction (Demougeot et al., 2004, J. Neurochem. 90, 776-83). Therefore, an NAA level, measured by $^1$H-MRS, is an useful indicator for following the effect of stem cell transplantation after cerebral ischemia.

One can also measure the expression level of a trophic factor or a cell death-related protein in a sample (e.g., cerebrospinal fluid) obtained from the animal before or after administration to confirm efficacy. The expression level can be determined at either the mRNA level or the protein level. Methods of measuring mRNA levels in a tissue sample or a body fluid are well known in the art. To measure mRNA levels, cells can be lysed and the levels of mRNA in the lysates, whether purified or not, can be determined by, e.g., hybridization assays (using detectably labeled gene-specific DNA or RNA probes) and quantitative or semi-quantitative RT-PCR (using appropriate gene-specific primers). Alternatively, quantitative or semi-quantitative in situ hybridization assays can be carried out on tissue sections or unlysed cell suspensions using detectably (e.g., fluorescent or enzyme) labeled DNA or RNA probes. Additional mRNA-quantifying methods include the RNA protection assay (RPA) method and the serial analysis of gene expression (SAGE) method, as well as array-based technologies.

Methods of measuring protein levels in a tissue sample or a body fluid are also well known in the art. Some of them employ antibodies (e.g., monoclonal or polyclonal antibodies) that bind specifically to a target protein. In such assays, the antibody itself or a secondary antibody that binds to it can be detectably labeled. Alternatively, the antibody can be conjugated with biotin. Its presence can be determined by detectably labeled avidin (a polypeptide that binds to biotin). Combinations of these approaches (including "multi-layer sandwich" assays) can be used to enhance the sensitivity of the methodologies. Some protein-measuring assays (e.g., ELISA or Western blot) can be applied to body fluids or to lysates of cells, and others (e.g., immunohistological methods or fluorescence flow cytometry) can be applied to histological sections or unlysed cell suspensions. Appropriate labels include radionuclides (e.g., $^{125}I$, $^{131}I$, $^{35}S$, $^{3}H$, or $^{32}P$), enzymes (e.g., alkaline phosphatase, horseradish peroxidase, luciferase, or β-glactosidase), fluorescent/luminescent agents (e.g., fluorescein, rhodamine, phycoerythrin, GFP, BFP, and Qdot™ nanoparticles supplied by the Quantum Dot Corporation, Palo Alto, Calif.). Other applicable methods include quantitative immunoprecipitation or complement fixation assays.

Based on the results from the assays described above, an appropriate dosage range and administration route can be determined. The dosage required depends on the choice of the route of administration; the nature of the formulation; the nature of the patient's illness; the subject's size, weight, surface area, age, and sex; other drugs being administered; and the judgment of the attending physician. Dosage variations are necessary in view of the different efficiencies of various routes of administration. The variations can be adjusted using standard empirical routines for optimization as is well understood in the art. Both heterologous and autologous HUCMSCs can be used. In the former case, HLA-matching should be conducted to avoid or minimize host reactions. In the latter case, autologous HUCMSCs are enriched and purified from a subject and stored for later use.

The specific examples below are to be construed as merely illustrative, and not limitative of the remainder of the disclosure in any way whatsoever. Without further elaboration, it is believed that one skilled in the art can, based on the description herein, utilize the present invention to its fullest extent. All publications cited herein are hereby incorporated by reference in their entirety. Further, any mechanism proposed below does not in any way restrict the scope of the claimed invention.

EXAMPLE 1

Human umbilical cord-derived mesenchymal stem cells (HUCMSCs) were isolated from the Wharton's jelly and characterized. The Wharton's jelly was previously shown to be composed of myofibroblast-like stromal cells (Kobayashi et al., 1998, Early Hum Dev 51, 223-33). Myofibroblasts include bone marrow stromal cells, astrocytes, and pericytes (Powell et al., 1999, Am. J. Physiol. 277, C1-9). They play important role in growth, development, and repairing.

Ten human umbilical cord samples of a mean gestational age of 38.9±1.1 weeks (20 cm in length, 20 gm in weight) were collected in sterile boxes containing a Hanks' balanced salt solution (HBSS; Gibco/BRL 14185-052) and subjected to characterization within 24 hours. Protocols for sampling human umbilical cords were approved by the Institutional Review Board. Written informed consent was obtained from each mother before labor and delivery.

For histology examination and immunphenotyping, the umbilical cord samples were immersed in 4% paraformaldehyde, dehydrated in 30% sucrose, and frozen on dry ice. A series of adjacent 10 µm-thick sections were cut in the coronal plane with a cryostat, stained with Hematoxylin-eosin (H&E), and observed under a light microscope (Nikon, E600). Immunostaining was performed by the labeled streptavidin-biotin (LSAB) method (DAKO LASB-2 Kit, Peroxidase, DAKO) according to the manufacture's guide and followed by incubation with appropriate diluted antibodies to CD13, CD29, CD44, CD90, CD34, CD45, or CD117 (dilution 1:200; BD, PharMingen) at room temperature for 1 hour.

H&E staining of the sections revealed two arteries and one vein surrounded by the Wharton's jelly. The cells in the Wharton's jelly showed a fibroblastic morphology with homogenous deposition of extracellular matrix. Immunostaining revealed strong positive signals of CD13, CD29, CD90, and CD44 and negative signals of CD34, CD45 and CD117. These results indicate that the cells were not of hematopoietic origin.

To obtain HUCMSCs, collected human umbilical cord tissues were washed three times with $Ca^{2+}$ and $Mg^{2+}$ free PBS (DPBS, Life technology) before being cut by scissors along the midline direction. Then, the vessels of umbilical artery, vein, and outlining membrane were dissociated from the Wharton's jelly. The Wharton's jelly was then extensively cut into many pieces smaller than 0.5 $cm^3$ and incubated with collagenase type 1 (Sigma, St Louis, USA) for 14-18 hours at 37° C. in a 95% air/5% $CO_2$ humidified atmosphere. The resulting explants were cultured in DMEM containing 10% human cord blood serum (CBS) and antibiotics at 37° C. in 95% air/5% $CO_2$ humidified atmosphere, and left undisturbed for 5-7 days to allow migration of cells from the explants. It was found that adherently growing cells of spindle-shape migrated from the explants and proliferate rapidly. The cells were then fed with a medium twice weekly and passed as necessary. These rapidly dividing cells were extensively expanded. It was found that they could be cultured for over 25 passages, equivalent to over 40 population doublings, without indications of spontaneous differentiation, senescence, morphological changes, increased growth rate, or changes in ability to differentiate into neurons.

Specific surface molecule of the cells of passage 4-8 generations were characterized by flow cytometric analysis. Briefly, the cells were detached with 2 mM EDTA-PBS, washed in PBS containing 2% BSA and 0.1% sodium azid (Sigma, USA), and incubated with antibodies conjugated with fluorescein isothiocyanate (FITC) or phycoerythrin (PE). The antibodies included anti-CD10, -CD13, -CD11b, -CD34, -CD90, -CD73, -CD105, -HLA-ABC, -HLA-DR, -CD14, -CD29, -CD44, -CD105, and -CD117 (BD, PharMingen). The cells were then analyzed using a Becton Dickinson flow cytometer (Becton Dickinson, San Jose, Calif.). It was found that the cells were negative for CD 34, CD45, and CD117, but positive for CD29, CD44, and CD49. These results demonstrated that the cells isolated from WJ of human umbilical cord possess the potential of mesenchymal stem cells (MSCs) consistent with the findings of bone marrow MSCs. Thus, they were named as HUCMSCs. Immunostaining of additional marks were conducted. The results were summarized in Table 1 below.

TABLE 1

Marker profile of HUCMSCs

| Positive | Negative |
|---|---|
| CD13 | CD34 |
| CD29 | CD45 |
| CD44 | CD117 (C-KIT) |
| CD49b | CD1q |
| CD90 | CD3 |
| CD73 | CD10 |
| CD105 | CD14 |
| CD166 | CD31 |
| HLA-ABC | CD49d |
|  | CD56 |
|  | HLA-DA |

To investigate the differentiation potential of HUCMSCs, fifth to tenth-passage cells were seeded at a density of $5 \times 10^3$ cells/cm$^2$ and induced to form neuro-glial cells, osteocyte, and adipocyte.

More specifically, HUCMSCs were passaged and cultured to confluence, shifted to an osteogenic medium (α-MEM supplemented with 10% CBS, 0.1 umol/l dexamethsson, 10 mmol/l β-glycerol phosphate, 50 umol/l ascorbate) or an adipogenic medium (α-MEM supplemented with 10% CBS, 1 umol/l dexamethasone, 5 ug/ml insulin, 0.5 mmol/l isobutyl-methylxanthine and 60 umol/l indomethacin), and incubated for 3 weeks. The differentiation potential for osteogenesis was assessed by the mineralization of calcium accumulation by von Kossa staining. For adipogenic differentiation, intracellular lipid droplets could be observed under the microscope and confirmed by Oil Red O staining.

For neural differentiation, HUCMSCs were incubated in α-MEM with serum supplement, 1 mmol/l β-mercaptoethanol, 5 ng/ml bFGF (Sigma, St Louis) for 7 days, and then subjected to serum depletion, and 10 mmol/l β-mercaptoethanol for 5 hours (Woodbury et al., 2000, J. Neurosci. Res. 61, 364-70). After 7 days of differentiation, half of the cells exhibited the morphology of refractile cell body with extended neuritelike structures arranged into a network. Immunocytochemical stain with neuron specific class III β-tubulin (Tuj-1), neurofilament and GFAP (dilution 1:300; Chemicon) was used to assess the capacity of neuronal differentiation. It was found that HUCMSCs-derived neuroglial cells could be identified by the immunostaining against Tuj-1, NF, or GFAP.

EXAMPLE 2

HUCMSCs were transplanted to repair brain tissue damage in rat brain ischemia/reperfusion models.

Adult male Sprague-Dawley rats (weighing 250-300 g) were subjected to three-vessel ligation. All surgical procedures were performed by sterile/aseptic techniques in accordance with institutional guidelines. The rats were anesthetized with chloral hydrate (0.4 g/kg, ip). Ligation of the right middle cerebral artery (MCA) and the bilateral common carotids (CCAs) was performed by a method modification from that described in Chen et al., 1986, Stroke 17, 738-43. The bilateral CCAs were clamped with nontraumatic arterial clips. Under a surgical microscope, a 2×2 mm craniotomy was drilled in the landmark where the zygoma fuses to the squamosal bone. The right MCA was ligated with a 10-0 nylon suture. Cortical blood flow was measured continuously with a laser Doppler flowmeter (PF-5010, Periflux system, Perimed AB, Stockholm, Sweden). A burr hole (1-mm diameter) was made in the right frontoparietal region to allow placement of photodetectors. A probe (0.45 mm in diameter) was stereotaxically placed in the cortex (1.3 mm posterior, 2.8 mm lateral to the bregma, and 1.0 mm below the dura). After 90 minutes of ischemia, the suture on the MCA and arterial clips on CCAs were removed to allow reperfusion. The temperature of the rat was maintained at 37° C. with a heating pad during anesthesia. The core body temperature was monitored using a thermistor probe. After recovery from the anesthesia, the body temperature was maintained at 37° C. with a heat lamp.

One week later, 20 rats that had received the above treatments were divided into two groups (10 in each). The rats in one group ("treated rats") were transplanted with HUCMSCs. The other rats ("control") received control treatment. More specifically, HUCMSCs were cultured in DMEM (Gibco, Grand Island, N.Y., USA) with 10% CBS and antibiotics at 37° C. in humidified 5% $CO_2$/95% air. Prior to transplantation, the cells were incubated with 1 μg/mL bisbenzimide (nuclei labeling with blue color fluorescence) (Hoechst 33342; Sigma, U.S.A.) for 5 hours at 37° C. Then, the labeled cells were collected and washed in PBS for three times. Nucleated HUMSCs were counted using a cytometer.

The above-described rats were anesthetized with chloral hydrate (0.4 g/kg, ip), and injected intracerebrally with approximately $1 \times 10^6$ cells in a 3-5 μl PBS suspension through a 26-gauge Hamilton syringe into 3 cortical areas adjacent to the right MCA, 3.0 to 5.0 mm below the dura. The approximate coordinates for these sites were 1.0 to 2.0 mm anterior to the bregma and 3.5 to 4.0 mm lateral to the midline, 0.5 to 1.5 mm posterior to the bregma and 4.0 to 4.5 mm lateral to the midline, and 3.0 to 4.0 mm posterior to the bregma and 4.5 to 5.0 mm lateral to the midline. The needle was retained in place for 5 minutes after each injection and a piece of bone wax was applied to the skull defects to prevent leakage of the injected solution. Rat hosts did not receive any immunosuppression.

Neurological behavioral measurements were performed 5 days before the cerebral ischemia, and 1, 7, 14 and 28 days after the cell transplantation. More specifically, body asymmetry and locomotor activity were examined.

The elevated body swing test was used to assess body asymmetry after MCA ligation and evaluated quantitatively according to the method described in Borlongan et al., 1998, Exp. Neurol. 149, 310-21. Initially, the rats were examined for lateral movement, their bodies being suspended by their tails $10^{-2}$ m above the ground. The frequency of initial head swing contra-lateral to the ischemic side was counted in twenty continuous tests and was normalized by the baseline score.

For locomotor activity, the rats were subjected to Versa-Max Animal activity monitoring (Accuscan Instruments, Inc., Columbus, Ohio) for about 2 hours for behavioral recording. This instrument contained 16 horizontal and 8 vertical infrared sensors spaced 87 cm apart. The vertical sensors were situated 10 cm from the floor of the chamber. Motor activity was counted as the number of beams broken by a rat movement in the chamber. Three parameters of vertical items over 2 hours were calculated: (i) vertical activity (ii) vertical time (iii) No. of vertical movement.

The behavioral measurement scores were all normalized by the baseline scores. Since cerebral ischemia causes imbalanced motor activity, all of the rats developed significant body asymmetry and turned contralateral to the side of the ischemic brain following cerebral ischemia. From 14 to 28 days after transplantation, rats treated with HUCMSCs, exhibited significantly reduced body asymmetry in comparison to that of controls. Vertical activity, vertical movement time and the number of vertical movements significantly increased between 14 and 28 days after cerebral ischemia in rats receiving HUCMSCs treatment. These results indicate that HUCMSCs transplantation improves neurological behavior of rats having cerebral ischemia.

To assess therapeutic potential of HUCMSCs, the above-described rats were imaged 3, 7, 14, and 28 days after intracerebral HUCMSCs injection. Magnetic resonance (MR) imaging was conducted on a 3.0-Tesla whole-body Signa EchoSpeed MR scanner (General Electric, Milwaukee, Wis.). Each rat was anesthetized with chloral hydrate (0.4 g/kg, ip) and was supported on a wooden cradle. Its head was placed in a birdcage coil with a 5-cm outer diameter. After the acquisition of scout images, six to eight coronal plane images were taken from between 3 mm behind the olfactory bulb and the caudal portion of the cerebellum. Each slice was 2 mm thick without any gaps, matrix size 320×160 and an 8×4 cm field of view. T2-weighted fast spin echo (FSE) sequences were optimized to detect the lesion size. The acquisition parameters were: TE/TR 105/4000 ms, echo train length 53, NEX 8. Each image was determined by a consensus of two observers blinded to the HUCMSCs injection. The MRI revealed larger infracted area in control rats than in the treated rats.

Proton Magnetic Resonance spectroscopy ($^1$H-MRS) was also conducted to evaluate effects of HUCMSC transplantation on neuronal metabolism at 3, 7, 14 and 28 days after intracerebral HUCMSCs transplantation. MRI was acquired from each rat in the same manner described above. $^1$H-MRS was performed on the same MRI scanner with a multi-voxel technique. T2-weighted transverse, coronal or sagittal images were used to localize the volume of interest (VOI). The VOI (0.5×0.5×0.5 cm) was precisely localized centrally to the infracted brain using two or three images (transverse and sagittal/coronal). The spectroscopic acquisition parameters were as follows: TR=3.0 sec/TE=30 msec and NS=36 AVG with PROton Brain Exam (PROBE) (GE Medical Systems). CHESS(CHEmical Shift Selective) sequence was used for suppression of the $H_2O$ signal. All raw data were transferred to a Sun Sparc-10 workstation (SUN Computer Inc., Sunnyvale, U.S.A.), and processed using Spectral Analysis/General Electric (SA/GE) software (GE Medical Systems) incorporating low frequency filtering of residual water signal, apodization by 0.5 Hz of exponential line broadening, zero-filling of 8 k, Fourier transformation, and lorenzian to gaussian transformation according to the scheme as described in Kreis et al., 1992, Radiology 182, 19-27. Metabolic peaks were fitted by the lorenzian line shape at known frequencies of N-acetylaspartate (NAA) at 2.02 ppm, creatine (Cr) at 3.03 ppm, choline and cholinecontaining compounds (Cho) at 3.22 ppm. The values of the [NAA/Cr] and [NAA/Cho] ratios were calculated. The result of the metabolic ratio was presented as mean±SE.

It was found that, in normal rat cerebral cortex, three important signals were consistently detected: choline (Cho), creatine (Cr) and N-acetyl-aspartate (NAA). In $^1$H-MRS of infarcted brains using multi-voxel technique, major changes were observed: a sharp decrease in NAA signaling together with a mild decrease in Cho and Cr. Four weeks after cell transplantation, significant improvements in neuronal activity were observed with regards to NAA/Cho and NAA/Cr (2.04±0.12 and 2.52±0.15, respectively) (n=6) in the treated group in comparison to NAA/Cho and NAA/Cr (1.71±0.13 and 1.90±0.17, respectively) (n=6) in the control group.

To determine whether transplanted HUCMSCs could differentiate into neurons, glial, or vascular endothelial cells at the ischemic sites, double fluorescent immunohistochemistry and laser scanning confocal microscopy were applied to analyze the co-localization of cell-type specific markers and bis-benzimide-labeled cell nuclei.

The rats were anesthetized with chloral hydrate (0.4 g/kg, ip) and their brains fixed by transcardial perfusion with saline, followed by perfusion and immersion with 4% paraformaldehyde. Finally, the brain samples were dehydrated in 30% sucrose. After brains were frozen on dry ice, a series of adjacent 6-µm-thick sections were cut in the coronal plane with a cryostat, stained with H&E and observed by light microscopy (Nikon, E600). For fluorescences analysis, blue color fluorescence (from bis-benzimide) of brain section was detected directly by fluorescence microscopy (Carl Zeiss, Axiovert 200M).

The above results indicate that intracerebrally transplanted HUCMSCs were found in the brain, and significantly more HUCMSCs were found in the ipsilateral hemisphere than in the contralateral hemisphere. Many cells migrated into the boundary zone of ischemic brain. HUCMSCs survive, and some express cell type-specific markers GFAP, NeuN and MAP-2. Most importantly, a significant improvement in motor function was found in stroke rats after receiving HUCMSCs. The mechanisms by which transplanted HUCMSCs led to functional improvement are not clear. Morphologic analysis indicates that HUCMSCs had the capacity to selectively migrate into the ischemic damaged rat brain. HUCMSCs survived and a scattered few cells expressed protein markers for parenchymal brain cells. Though HUCMSCs may have the potential to replace lost neurons, it is likely that the mechanisms providing therapeutic benefit are multipronged.

The above studies also demonstrate that HUCMSCs differentiate into cerebral endothelial cells in rats having cerebral infarction. The relatively large number of HUCMSCs lining the vasculature suggests that they make a significant contribution to the neovascularization that occurs after a cerebral infarction. These Hoechst 33342-labeled HUCMSCs had the morphological characteristics of endothelial cells and co-expressed the von Willebrand factor, confirming their identification as endothelial cells. There were only rare HUCMSCs evident in vessels in normal or noninfarcted brain, suggesting that under normal physiological conditions, HUCMSCs rarely differentiate into endothelium. The rarity of HUCMSCs at 1 day after MCA occlusion suggests that the grafted HUCMSCs have not had sufficient time to be recruited to the damaged vessels. However, by 3 days after MCA occlusion, significant numbers of HUCMSCs were participating in vasculogenic repair of the blood vessels. HUCMSCs may "home" in onto the damaged tissues. In a model of hepatic injury, regenerated hepatic cells were shown to be of bone marrow origin (Petersen et al., 1999, Science 284, 1168-70). These findings suggest that the "injured" brain might specifically attract HUCMSCs or those HUCMSCs might "home in" on the injured brain. Regeneration of the brain after cerebral ischemia requires not only the generation of new blood vessels but also the generation of neurons and glial cells.

Interestingly, although only a small percentage of the HUCMSCs expressed markers of neuronal, astrocytic, or endothelial cells, functional recovery was found 14 days after transplantation. It is highly unlikely that these cells integrated into the cerebral tissue and made appropriate connections within days after transplantation. Therefore, a more likely mechanism of short-term benefit is that the HUCMSCs supplemented compromised tissues with cytokines and/or growth factors that promote a functional recovery of the remaining neurons and reduce apoptosis in the ischemic boundary zone.

EXAMPLE 3

To demonstrate the differentiation potential of transplanted cells, the expression of cell type-specific markers in bisbezimide-labeled HUCMSCs were examined by immunofluorescent analysis. Cell-type specific marker examined included glial fibrillary acidic protein (GFAP), von Willebrand factor (vWF), Nestin, microtubule-associated protein 2 (MAP-2) and neuronal nuclei (Neu-N). Each coronal section was immunoassayed with cell-specific antibodies: GFAP (for astrocyte, 1:400, Sigma), MAP-2 (for neuronal dendrites, 1:200; BM), Nestin (for neuron body, 1:400, Sigma), vWF (for endothelial cell, 1:20, Sigma), neuronal nuclear antigen (Neu-N for neuronal nuclei, 1:200, Chemicon), CXCR4 (CD 184, 1:100, Torrey Pines Biolab) and Doublecortin (Dcx, 1:100, Santa Cruz Biotechnology) conjugated with Cy-3 (Jackson Immunoresearch PA USA, 1:500 to determine that they colocalized bis-benzimide in the same cells. The stained tissue sections were examined under a Carl Zeiss LSM510 laser-scanning confocal microscope. It was found that in some cells, blue signal (bisbenzimide) co-localized with red signal (Cy3-MAP-2, Nestin, Neu-N, GFAP, vWF and CXCR4). The total number of doubled labeled cells (i.e., differentiated cells) was determined by the method described in Li, Neurology 2002; 59:514-523.

The results show that some bis-benzimide labeled cells colocalized with antibodies for GFAP, MAP-2, and Neu-N in the penumbra area of HUCMSCs treated ischemic rat brains. Co-localization of bisbenzimide-labeled cells with Nestin was also found in the peri-infarcted area of the ischemic brain. Linear axonal immunofluorescent staining of Nestin indicated an extended neurite outgrowth from the transplanted stem cells to construct anatomical synaptic connection between the grafted cells and the original recipient rat brain neuron. Some bis-benzimide labeled cells also showed vascular phenotypes (vWF+) and were found around the perivascular and endothelial regions in the ischemic hemispheres of the HUCMSCs-treated rats. Percentages of bisbenzimide-labeled cells co-localizing with specific markers MAP-2, GFAP, Neu-N, Nestin, and vWF were about 6%, 9%, 6%, 3%, 5%, respectively. These findings indicate that HUCMSCs could trans-differentiate and generate new neural and vascular tissues to repair injured areas of brain.

To demonstrate stem cells homing and migration, doubling immunofluorescence of specific markers CXCR4 and Dcx was performed in the same manner. It was found that a larger proportion (~50%) of transplanted HUCMSCs (bisbenzimide positive) near the penumbra region expressed CXCR4. Dcx was also found surrounding the ischemic region. These results indicate that the transplanted stem cells migrate to home in on the penumbra area and repair the injured brain.

Semi-quantitative RT-PCR was conducted to examine expression of mRNA species encoding factors known to protect the ischemic cortical areas (n=4). Rats were anesthetized with chloral hydrate (0.4 g/kg, ip) seven days after cell transplantation. Ischemic cortical and striatal areas were obtained and put on ice immediately. The brain tissues were homogenized by a stainless homogenizer in a buffer containing 1 g/ml (Promega, USA) and total RNA was extracted using the total RNA extraction kit, TRIZOL™ (Invitrogen, USA). The extraction procedure was done according to the manufacture's protocol. More specifically, cDNA was synthesized from 3 µg of total RNA in a mixture of 12 µl RNA and 1 µl primer mixture, which contained 0.5 µg/µl Oligo(dT) and DEPC water. The mixture was incubated at 70° C. for 10 minutes before mixed with 2 µl of 10× reverse transcriptase (RT) buffer, 1 µl of four kinds of dexoxynucleotide triphosphate at 10 mM, 2 µl of 0.1 M DTT, 2 µl of 25 mM $MgCl_2$, and adjusted to a final volume of 19 µl. The RT reaction was started by adding 1 µl of SUPERSCRIPT II™ (Invitrogen, USA) reverse transcriptase. This reaction was carried out at 42° C. for 60 minutes and terminated by heating at 90° C. for 5 minutes and soaking at 4° C. The following neurotrophic factors were studied stromal-cell-derived factor-1 (SDF-1), FGF-II, TGF-β, NGF, BDNF, GDNF and VEGF. The corresponding primers and amplicon sizes were listed in Table 2. GAPDH was used as an internal control for the RT-PCR. The sense primer for GADPH was 5'-GGCTGTGTGTCCCTG-TAT-3' (SEQ ID NO:15) and the anti-sense primer 5'-CCGCTCATTGCCGATAGTG-3' (SEQ ID NO:16).

TABLE 2

Sequence of PCR primers for neurotrophic factors

| Factors | Sequence | SEQ ID NO: | PCR Fragment |
|---------|----------|------------|--------------|
| SDF-1 | sense-TTGCCAGCACAAAGACACTCC | 1 | 243 bp |
|  | anti-sense-CTCCAAAGCAAACCGAATACAG | 2 |  |
| BDNF | sense-CAGTGGACATGTCCGGTGGGACGGTC | 3 | 533 bp |
|  | anti-sense-TTCTTGGCAACGGCAACAAACCA-CAAC | 4 |  |
| GDNF | sense-CCACACCGTTTAGCGGAATGC | 5 | 638 bp |
|  | anti-sense-CGGGACTCTAAGATGAAGTTATGGG | 6 |  |
| NGF | sense-GTTTTGGCCAGTGGTCGTGCAG | 7 | 498 bp |
|  | anti-sense-CCGCTTGCTCCTGTGAGTCCTG | 8 |  |

TABLE 2-continued

Sequence of PCR primers for neurotrophic factors

| Factors | Sequence | | SEQ ID NO: | PCR Fragment |
|---|---|---|---|---|
| TGF-β | sense- | CCGCCTCCCCCATGCCGCCC | 9 | 710 bp |
| | anti-sense- | CGGGGCGGGGCTTCAGCTGC | 10 | |
| FGF-II | sense- | TCACTTCGCTTCCCGCACTG | 11 | 252 bp |
| | anti-sense- | GCCGTCCATCTTCCTTCATA | 12 | |
| VEGF | sense- | GCTCTCTTGGGTGCACTGGA | 13 | 431 bp |
| | anti-sense- | CACCGCCTTGGCTTGTCACA | 14 | |

The results revealed significantly increased expression of SDF-1 and BDNF in a time-dependent manner in the ischemic rats transplanted with stem cells in comparison to the non-ischemic and vehicle controls. The ratio of SDF-1 or BDNF to GAPDH peaked at about a 2-fold increase in comparison to the control 14 days after transplantation of stem cells.

Growth factors and cytokines are molecular signals that regulate cell survival, proliferation and differentiation (Yoshimura, et al., 2001, Proc. Natl. Acad. Sci. USA 98, 5874-9. It has been found that exogenously administered neurotrophic growth factors may limit the extent of acute ischemic neural injury and enhance functional recovery after stroke (Ay et al., 2001, Brain Res. Mol. Brain. Res. 87, 71-80. It has been reported that transplantation of cells, such as rodent embryonic hippocampal formation cells and human neuroteratocarcinoma derived neuron ameliorates neurological deficits induced by brain ischemia (Netto et al., 1993, Behav. Brain Res. 58, 107-12; Onifer et al., 1990, Prog. Brain Res. 82, 359-66; Borlongan, et al., 1998, Exp. Neurol 149, 310-21; Saporta et al., 1999, Neuroscience 91, 519-25; and Kondziolka et al., 2000, Neurology 55, 565-9). MSCs from bone marrow express many cytokines known to play a role in hematopoiesis and also supply autocrine, paracrine, and juxtacrine factors that influence cells of the marrow microenvironment (Haynesworth et al., 1996, J. Cell Physiol. 166, 585-92; and Dormady et al., 2001, J. Hematother. Stem Cell Res. 10, 125-40.

Thus, HUCMSCs may, in addition to directly promoting plasticity of the ischemic damaged neurons, involve in stimulating the expression and secretion of growth factors or cytokines (e.g., BDNF and NGF). It is possible that the grafted HUCMSCs migrated to injured tissue and provided neurotrophic factors, and that the interaction of HUCMSCs with the host brain resulted in production of additional neurotrophic factors by the HUCMSCs or parenchymal cells (Hefti, 1986, J Neurosci. 6, 2155-62 (1986). It is likely that HUCMSCs within the cerebral tissues express these factors, and it is the effect of these cytokines and trophic factors on brain tissue which rapidly and effectively promotes restoration of neuronal function. The interaction between HUCMSCs and the ischemic brain enhances the secretion of neurotrophins which may reduce neuronal apoptosis in the ischemic boundary zone and promote cell proliferation from the relatively intact SVZ in the ischemic brain. Indeed, double immunofluorescent studies demonstrated linear axonal immunofluorescent staining of Nestin, indicating extended neurite outgrowth from the transplanted stem cells to construct anatomical synaptic connection between the grafted cells and original recipient rat brain neuron.

OTHER EMBODIMENTS

All of the features disclosed in this specification may be combined in any combination. Each feature disclosed in this specification may be replaced by an alternative feature serving the same, equivalent, or similar purpose. Thus, unless expressly stated otherwise, each feature disclosed is only an example of a generic series of equivalent or similar features.

From the above description, one skilled in the art can easily ascertain the essential characteristics of the present invention, and without departing from the spirit and scope thereof, can make various changes and modifications of the invention to adapt it to various usages and conditions. Thus, other embodiments are also within the scope of the following claims.

What is claimed is:

1. A method of treating a brain tissue injury resulting from cerebral ischemia, comprising administering to a subject in need thereof a composition containing a plurality of cultured pluripotent cells that are CD13+, CD90+, and CD117−, resulting in an improved neurological behavior or brain metabolic activity in the subject as compared to before the treatment, wherein the cultured pluripotent cells are produced by the following procedure:
   obtaining Wharton's jelly from an umbilical cord of a human;
   culturing the Wharton's jelly in DMEM containing 10% human cord blood serum to allow cells to migrate out of the Wharton's jelly; and
   culturing the cells that migrated out of the Wharton's jelly to obtain the cultured pluripotent cells.

2. A method of treating neurodegeneration resulting from cerebral ischemia, the method comprising:
   identifying a subject suffering from or being at risk for developing neurodegeneration resulting from cerebral ischemia, and
   administering to the subject a composition containing a plurality of cultured pluripotent animal cells that are CD13+, CD90+, and CD 117−, resulting in an improved neurological behavior or brain metabolic activity in the subject as compared to before the treatment;
   wherein the cultured pluripotent cells are prepared by the following procedure:
   obtaining Wharton's jelly from an umbilical cord of a human;
   culturing the Wharton's jelly in DMEM containing 10% human cord blood serum to allow cells to migrate out of the Wharton's jelly; and
   culturing the cells that migrated out of the Wharton's jelly to obtain the cultured pluripotent cells.

3. A method of increasing the expression level of a neurotrophic factor in the brain of a subject suffering from cerebral ischemia, comprising administering to a subject in need thereof a composition containing a plurality of cultured pluripotent animal cells that are CD13+, CD90+, and CD117− resulting in an increased level of expression of a neurotrophic factor in the subject as compared to non-ischemic and vehicle controls, wherein the cultured pluripotent cells are prepared by the following procedure:
   obtaining Wharton's jelly from an umbilical cord of a human;
   culturing the Wharton's jelly in DMEM containing 10% human cord blood serum to allow cells to migrate out of the Wharton's jelly; and
   culturing the cells that migrated out of the Wharton's jelly to obtain the cultured pluripotent cells;
   wherein the expression level of the neurotrophic factor is measured in a biological sample obtained from the subject.

4. The method of claim 3, wherein the neurotrophic factor is brain-derived neurotrophic factor, glial-cell line derived neurotrophic factor, nerve growth factor, stromal cell derived factor-1, transforming growth factor, fibroblast growth factor, or vascular endothelial growth factor.

5. The method of claim 1, wherein the cells are administered at $1\times10^4$ to $1\times10^7$/dose.

6. The method of claim 5, wherein the cells are administered at $1\times10^5$ to $5\times10^6$/dose.

7. The method of claim 6, wherein the cells are administered at $5\times10^5$ to $2\times10^6$/dose.

8. The method of claim 1, wherein the cells are autologous to the subject.

9. The method of claim 1, wherein the cells are administered intracerebrally.

10. The method of claim 3, wherein the biological sample is cerebrospinal fluid.

11. The method of claim 1, wherein the subject is a human subject.

12. The method of claim 2, wherein the subject is a human subject.

13. The method of claim 3, wherein the subject is a human subject.

* * * * *

SEQUENCE LISTING

<160> NUMBER OF SEQ ID NOS: 16

<210> SEQ ID NO 1
<211> LENGTH: 21
<212> TYPE: DNA
<213> ORGANISM: Artificial Sequence
<220> FEATURE:
<223> OTHER INFORMATION: Primer

<400> SEQUENCE: 1

-continued ttgccagcac aaagacactc c                                              21

<210> SEQ ID NO 2
<211> LENGTH: 22
<212> TYPE: DNA
<213> ORGANISM: Artificial Sequence
<220> FEATURE:
<223> OTHER INFORMATION: Primer

<400> SEQUENCE: 2
ctccaaagca aaccgaatac ag                                             22

<210> SEQ ID NO 3
<211> LENGTH: 26
<212> TYPE: DNA
<213> ORGANISM: Artificial Sequence
<220> FEATURE:
<223> OTHER INFORMATION: Primer

<400> SEQUENCE: 3
cagtggacat gtccggtggg acggtc                                         26

<210> SEQ ID NO 4
<211> LENGTH: 27
<212> TYPE: DNA
<213> ORGANISM: Artificial Sequence
<220> FEATURE:
<223> OTHER INFORMATION: Primer

<400> SEQUENCE: 4
ttcttggcaa cggcaacaaa ccacaac                                        27

<210> SEQ ID NO 5
<211> LENGTH: 21
<212> TYPE: DNA
<213> ORGANISM: Artificial Sequence
<220> FEATURE:
<223> OTHER INFORMATION: Primer

<400> SEQUENCE: 5
ccacaccgtt tagcggaatg c                                              21

<210> SEQ ID NO 6
<211> LENGTH: 25
<212> TYPE: DNA
<213> ORGANISM: Artificial Sequence
<220> FEATURE:
<223> OTHER INFORMATION: Primer

<400> SEQUENCE: 6
cgggactcta agatgaagtt atggg                                          25

<210> SEQ ID NO 7
<211> LENGTH: 22
<212> TYPE: DNA
<213> ORGANISM: Artificial Sequence
<220> FEATURE:
<223> OTHER INFORMATION: Primer

<400> SEQUENCE: 7
gttttggcca gtggtcgtgc ag                                             22

<210> SEQ ID NO 8
<211> LENGTH: 22
<212> TYPE: DNA
<213> ORGANISM: Artificial Sequence

```
<220> FEATURE:
<223> OTHER INFORMATION: Primer

<400> SEQUENCE: 8
ccgcttgctc ctgtgagtcc tg                                              22

<210> SEQ ID NO 9
<211> LENGTH: 20
<212> TYPE: DNA
<213> ORGANISM: Artificial Sequence
<220> FEATURE:
<223> OTHER INFORMATION: Primer

<400> SEQUENCE: 9
ccgcctcccc catgccgccc                                                 20

<210> SEQ ID NO 10
<211> LENGTH: 20
<212> TYPE: DNA
<213> ORGANISM: Artificial Sequence
<220> FEATURE:
<223> OTHER INFORMATION: Primer

<400> SEQUENCE: 10
cggggcgggg cttcagctgc                                                 20

<210> SEQ ID NO 11
<211> LENGTH: 20
<212> TYPE: DNA
<213> ORGANISM: Artificial Sequence
<220> FEATURE:
<223> OTHER INFORMATION: Primer

<400> SEQUENCE: 11
tcacttcgct tcccgcactg                                                 20

<210> SEQ ID NO 12
<211> LENGTH: 20
<212> TYPE: DNA
<213> ORGANISM: Artificial Sequence
<220> FEATURE:
<223> OTHER INFORMATION: Primer

<400> SEQUENCE: 12
gccgtccatc ttccttcata                                                 20

<210> SEQ ID NO 13
<211> LENGTH: 20
<212> TYPE: DNA
<213> ORGANISM: Artificial Sequence
<220> FEATURE:
<223> OTHER INFORMATION: Primer

<400> SEQUENCE: 13
gctctcttgg gtgcactgga                                                 20

<210> SEQ ID NO 14
<211> LENGTH: 20
<212> TYPE: DNA
<213> ORGANISM: Artificial Sequence
<220> FEATURE:
<223> OTHER INFORMATION: Primer

<400> SEQUENCE: 14
caccgccttg gcttgtcaca                                                 20
```

-continued

```
<210> SEQ ID NO 15
<211> LENGTH: 18
<212> TYPE: DNA
<213> ORGANISM: Artificial Sequence
<220> FEATURE:
<223> OTHER INFORMATION: Primer

<400> SEQUENCE: 15
ggctgtgtgt ccctgtat                                                 18

<210> SEQ ID NO 16
<211> LENGTH: 19
<212> TYPE: DNA
<213> ORGANISM: Artificial Sequence
<220> FEATURE:
<223> OTHER INFORMATION: Primer

<400> SEQUENCE: 16
ccgctcattg ccgatagtg                                                19
```